(12) United States Patent
Schlueter et al.

(10) Patent No.: US 9,874,513 B2
(45) Date of Patent: Jan. 23, 2018

(54) METHOD OF MEASURING ISOTOPE RATIO

(71) Applicant: Thermo Fisher Scientific (Bremen) GmbH, Bremen (DE)

(72) Inventors: Hans-Juergen Schlueter, Bremen (DE); Oliver Kracht, Bremen (DE); Jens Radke, Bremen (DE); Benno Strasser, Bremen (DE); Johannes Schwieters, Bremen (DE); Eric Wapelhorst, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/035,736

(22) PCT Filed: Nov. 10, 2014

(86) PCT No.: PCT/EP2014/074188
§ 371 (c)(1),
(2) Date: May 10, 2016

(87) PCT Pub. No.: WO2015/067806
PCT Pub. Date: May 14, 2015

(65) Prior Publication Data
US 2016/0266031 A1    Sep. 15, 2016

(30) Foreign Application Priority Data
Nov. 11, 2013    (GB) .................................. 1319875.9

(51) Int. Cl.
*G01N 21/00*    (2006.01)
*G01N 21/27*    (2006.01)
(Continued)

(52) U.S. Cl.
CPC ........... *G01N 21/276* (2013.01); *G01N 21/31* (2013.01); *G01N 33/004* (2013.01);
(Continued)

(58) Field of Classification Search
CPC ........... G01N 21/3504; G01N 33/0006; G01N 21/31; G01N 33/004; G01N 21/276;
(Continued)

(56) References Cited

U.S. PATENT DOCUMENTS 4,866,270 A    9/1989    Hall et al.
5,077,469 A    12/1991    Fabinski et al.
(Continued)

FOREIGN PATENT DOCUMENTS

CN    101936964 A    1/2011
CN    102175641 A    9/2011
(Continued)

OTHER PUBLICATIONS

Anonymous, "Guidelines for Achieving High Accuracy in Isotope Dilution Mass Spectrometry (IDMS)", Royal Society of Chemistry (2002), XP055168446, ISBN: 978-0-85-404418-4, pp. 1-34.
(Continued)

*Primary Examiner* — Michael P Stafira
(74) *Attorney, Agent, or Firm* — David A. Schell (57) ABSTRACT

An isotope ratio of a continuous sample is measured in an isotope ratio spectrometer. At least one sample isotope ratio is measured over a measurement time period $t''_s$, ($n \geq 1$) and a sample concentration $c''_s$ is measured over at least a part of the measurement time period $t''_s$. A reference gas concentration $c''_{ref}$ for the spectrometer is selected for reference to the sample measured during the measurement time period $t''_s$, on the basis of the measured sample concentration $c''_{ref}$. An isotope ratio of the reference gas is measured at the selected reference gas concentration $c''_{ref}$ in the spectrometer. The at least one isotope ratio of the sample measured during the measurement time period $t''_s$ is calibrated using the measured isotope ratio of the reference gas at the corresponding reference gas concentration $c''_{ref}$ and a plu-
(Continued)

rality of calibrated isotope ratios and a plurality of sample gas concentration measurements are determined, each being for a different time.

21 Claims, 7 Drawing Sheets

(51) Int. Cl.
*H01J 49/00* (2006.01)
*G01N 33/00* (2006.01)
*G01N 21/31* (2006.01)
*G01N 21/3504* (2014.01)

(52) U.S. Cl.
CPC ...... *G01N 33/0006* (2013.01); *H01J 49/0009* (2013.01); *G01N 21/3504* (2013.01)

(58) Field of Classification Search
CPC .... G01N 21/39; G01N 21/00; G01N 33/0004; G01N 33/497; G01N 2030/8405; G01N 30/7206; G01N 2021/3595; G01N 2021/399
See application file for complete search history.

(56) References Cited

U.S. PATENT DOCUMENTS

| | | | |
|---|---|---|---|
| 5,964,712 A | 10/1999 | Kubo et al. | |
| 2003/0216660 A1 | 11/2003 | Ben-Oren et al. | |
| 2008/0260587 A1* | 10/2008 | Coleman | G01N 30/88 422/89 |
| 2010/0198736 A1* | 8/2010 | Marino | G01N 21/3504 705/308 |

FOREIGN PATENT DOCUMENTS

| | | |
|---|---|---|
| GB | 2513120 A | 10/2014 |
| JP | H03-206943 A | 9/1991 |
| JP | H09-105714 A | 4/1997 |
| JP | H10-339669 A | 12/1998 |

OTHER PUBLICATIONS

Milton, et al., "High accuracy method for isotope dilution mass spectrometry with application to the measurement of carbon dioxide", International Journal of Mass Spectrometry 218 (2002), pp. 63-73.

Tuzson, et al., "High precision and continuous field measurements of $\delta 13C$ and $\delta 18O$ in carbon dioxide with a cryogen-free QCLAS", Appl. Phys. B 92 (2008), 451-458.

* cited by examiner

METHOD OF MEASURING ISOTOPE RATIO

FIELD OF THE INVENTION

This invention relates to a method for measuring an isotope ratio in an isotope ratio analyzer.

BACKGROUND OF THE INVENTION

Isotope-ratio analysis is used to measure the relative abundance of isotopes (isotope ratio) in a sample, which may be solid, liquid or gaseous and for a wide variety of elements. For instance, it is used for determining the isotope ratios $^{13}C/^{12}C$ and/or $^{18}O/^{16}O$ from $CO_2$, such as in air. Isotope-ratio analysis is most commonly performed by mass spectrometry (MS) but may also be performed by optical spectrometry.

For optical spectrometry, an isotope ratio is generally determined in a measurement cell of the spectrometer by measuring two separate spectral absorption lines, typically in the infrared region, one line for each different isotopic species (isotopologue), e.g. an absorption line for $^{12}C^{16}O_2$ and another line for $^{13}C^{16}O_2$. A convenient absorption line for $CO_2$ is the line at or about 4.3218 µm. If more lines are available per isotope (e.g. a doublet or triplet) it is possible to measure and use the information from more than one line, e.g. for other gases than $CO_2$ or in other spectral ranges that might be interesting. The ratio of the intensities of the spectral absorption lines is a measure of the ratio of the abundance of each of the isotopic species (and hence the isotope ratio, e.g. $^{13}C/^{12}C$). The outputs of the spectrometer are thus ratios of different isotopic lines (e.g. $R_{13C}=c_{13c}/c_{12c}$). The result is referenced against international standards using the established delta notation for isotope ratio reporting (e.g. $\delta_{13C}$ [‰]).

A general review of isotope ratio mass spectrometry and gas inlet systems can be found in Brenna et al, Mass Spectrometry Reviews, 1997, 16, 227-258.

In isotope ratio spectroscopy, a sample should be measured against a working standard, that is, one or more reference gases of known isotopic ratio. Typically the concentration of the sample and the working standard differ by between 10 parts per million (ppm), per minute, in ambient measurements, and up to 40 pp/min for plant chamber experiments.

It is observed that the measured isotope ratio depends upon the concentration of the analyte. Therefore a calibration factor (also termed a linearity calibration or concentration dependence), which depends upon the, for example, $CO_2$ concentration is used for each isotope ratio. It is known to employ one or more reference gases (that is, either one reference gas or a plurality of reference gases) each at a constant (known) concentration. The concentration of each reference gas is selected on the basis of a known concentration range of the sample, and usually provided in the form of reference gas mixtures in gas tanks. To calculate the linearity calibration factors, the spectrometer measures the gas (for instance $CO_2$) with the same isotopic ratio at different concentrations, or at least numerous reference gases with known isotope ratio and concentration are provided.

To provide the sample and reference at the same intensity (concentration) in gas isotope mass spectrometry, a classical solution has been the use of adjustable bellows and a changeover valve. (for example, see: Halsted R. E. & Nier A. O., 1950, Gas flow through the mass spectrometer viscous leak, Rev. Sci. Instrum., 21: 1019-1021; Or Habfast K. (1997) Advanced isotope ratio mass spectrometry I: Magnetic isotope ratio mass spectrometers; and In: Modern isotope ratio mass spectrometry, I. T. Platzner (ed.), John Wiley & Sons, Chichester, UK: 11-82). In this way, discrete samples are measured, after filling them into a reservoir. At the beginning of a measurement, the intensities from both reservoirs are matched by changing the volume of (and thereby the pressure within) one or both adjustable reservoirs.

Another system for calibrating the isotope ratio measurements to account for concentration dependence and a delta scale contraction is described in B. Tuzson et al, "High precision and continuous field measurements of $\delta^{13}C$ and $\delta^{18}O$ in carbon dioxide with a cryogen-free QCLAS", Appl. Phys. B (2008), Volume 92, pp 451-458. However, a drawback with the system described in Tuzson et al is that it utilises a significant number of separate diluted supplies of reference gases of known isotope ratio. Such reference gas/air mixtures are not commonly available when working in the field for example. Furthermore, the system described Tuzson et al does not employ a sample dilution.

U.S. Pat. No. 7,810,376 describes an aperture to keep the partial pressure of an analyte diluted in a carrier constant by feeding back the concentration information of the sensor in a flow controller to adjust the gas flow constant. Any changes in the sample concentration are removed by diluting the sample, such that the sample concentration of the measured sample is kept constant. The concentration information is therefore lost. The working standard concentration is also kept constant by a flow controller.

WO-2007/112876 describes a unit which keeps the sample gas concentrations constant by means of flow control devices and open splits by using the sensor signal to adjust valves. In general, samples are measured discretely, with the sample being burnt in a reactor and analysed by gas chromatography before isotope ratio analysis is performed. In this case, the carrier gas (such as Helium) flow is controlled to keep the concentration of sample and/or reference gases constant. This allows a single isotope ratio for each gas chromatograph peak to be determined. Sample concentration information is not relevant.

An improved arrangement for performing calibrations, which are required to calculate a δ-value from a ratio of spectral intensities, is described in our co-pending patent applications GB1306806.9, GB1306807.7 and GB1306808.5, the contents of which are incorporated herein by reference in their entirety.

Although calibration improves the concentration dependency of isotopic ratio analysis by a factor of between 5 and 10, further improvements in the accuracy of calibration would be desirable.

SUMMARY OF THE INVENTION

The present invention seeks to provide an improved method for measuring an isotope ratio of a continuous sample in an isotope ratio spectrometer, especially a calibrated isotope ratio.

It has been observed that the correlation between isotope ratio and concentration is not stable (that is, it varies over time and with changes in temperature). The present invention seeks to address a drift in system parameters by monitoring a change in the continuous sample concentration over time and adjusting the reference gas concentration at repeated intervals so that the sample and reference gas concentrations more closely follow each other over the course of a sample analysis. Multiple sample δ values and concentration values may thereby be obtained. The process is preferably iterative.

To comply with the principle of identical treatment, the concentration of an unknown sample gas should match with the concentration of the known reference (working standard). In experiments the sample concentration varies in the range of 10 ppm/min for ambient measurements and up to 40 ppm/min for plant chamber experiments therefore it is desirable that the working standard follows the sample concentration. A linear approximation between two references is used to compensate instrument drifts and concentration changes between two references as long as these effects are expected to be linear or nearly linear. The concentration information is desirably maintained; therefore a dilution of the sample may not be an option.

There is provided, in a first aspect, a method of measuring an isotope ratio of a continuous sample in an isotope ratio spectrometer comprising: a) measuring at least one sample isotope ratio over a measurement time period $t_s^n$ (n≥1) in the spectrometer; b) measuring a sample concentration $c_s^n$ over at least a part of the measurement time period $t_s^n$; c) selecting a reference gas concentration $c_{ref}^n$ for the spectrometer for reference to the sample measured during the measurement time period $t_s^n$, on the basis of the measured sample concentration $c_s^n$ during measurement time period $t_s^n$; d) measuring an isotope ratio of the reference gas at the selected reference gas concentration $c_{ref}^n$ in the spectrometer; and e) calibrating the at least one isotope ratio of the sample measured during the measurement time period $t_s^n$, having a sample concentration $c_s^n$, using the measured isotope ratio of the reference gas at the corresponding reference gas concentration $c_{ref}^n$. The measurement of the sample concentration $c_s^n$ may use a time-based statistic, such as a time-based average. This technique may be implemented in a variety of different ways to achieve some or all of the advantages noted above.

Typically in the known arrangements referred to above, discrete samples are measured. These may be volumes of gasses acquired from remote sites and/or they may be gas samples created from reactors or eluted from gas chromatographic columns. Gas samples collected may be stored in volumes and released to the analyzer over periods of time, presenting substantially the same sample concentration to the analyzer during the entire analysis time. Gases released from reaction events, or from gas chromatographic columns present varying concentrations over time to the analyzer. However in all these cases, a single isotope ratio is characteristic of the samples. In contrast to this, the present invention concerns continuous samples in which both the isotope ratio of gases present in the sample varies over time and the gas concentration varies over time. This variation is the subject of the analysis. Samples may, in this case, be measured over hours, days or even weeks, and multiple isotope ratio and concentration measurements are taken. Isotope ratio measurements may be taken every few minutes for time periods of weeks, and hence many thousands of measurements may be made.

Preferably, the method further comprises: f) determining a plurality of calibrated isotope ratios and a plurality of sample gas concentration measurements, each of the plurality of calibrated isotope ratios and the plurality of sample gas concentration measurements being for a different, respective time. This means that multiple calibrated sample isotope ratio measurements together with multiple sample concentration measurements are obtained over time. Advantageously, this allows both the variation of sample isotope ratio and concentration measurements to be measured against time, which can be especially useful for many different applications, as will be discussed below, but particularly those where a large-scale long-term variation in sample concentration may be possible. By matching the reference concentration to the sample (and not diluting the sample), the sample concentration information is retained and can be measured, which can be particularly desirable where that variation is of interest. Moreover, continuous sample monitoring allows a time-based analysis to be used.

This may be achieved by carrying out the step c) of selecting a reference gas concentration $c_{ref}^n$ for the spectrometer for reference to the sample measured during the measurement time period $t_s^n$ on the basis of the measured sample concentration $c_s^n$ (that is measured during at least a part of measurement time period $t_s^n$). This allows the reference gas concentration to be matched to a sample gas concentration, which varies dynamically over the measurement time period $t_s^n$. Step d) of measuring the isotope ratio of the reference gas at the reference gas concentration $c_{ref}^n$ in the spectrometer is therefore carried out with the reference gas concentration $c_{ref}^n$ matched to the measured sample concentration $c_s^n$. As a consequence, the step e) of calibrating the at least one isotope ratio of the sample using the measured isotope ratio of the reference gas results in a more accurate calibration and a wider range of sample concentration variation can be accommodated.

As noted above, the sample concentration changes dynamically. This may be an important consideration with a continuous sample that has previously been deemed not relevant to the calibration of the isotope ratio measured for the sample. The sample concentration varies over the course of the measurement time period $t_s^n$ significantly. Additionally, the sample concentration during a first measurement time period may be different from the sample concentration during a second, subsequent measurement time period $t_s^{n+1}$ (n≥1). For these reasons (and others noted below), the process is preferably repeated iteratively. For example, the method may further comprise iteratively repeating steps (a) to (e) for n=n+1, n+2 . . . so that, during a certain measurement time period $t_s^n$ (n≥1), the selected concentration of the reference gas during that certain measurement time period $t_s^n$ based upon the measured sample concentration during that certain measurement time period $t_s^n$. The selected concentration of the reference gas during that certain measurement time period may also be based upon the measured sample concentration during a preceding measurement time period $t_s^{n-1}$ and this will be discussed further below. Advantageously, the step f) of determining the plurality of calibrated isotope ratios and the plurality of sample gas concentration measurements comprises associating the at least one calibrated isotope ratio and the measured sample concentration for each measurement time period $t_s^n$ (n≥1), with a time from the respective measurement time period $t_s^n$. Thus, each measurement time period $t_s^n$ results in one or more calibrated sample isotope ratio measurements and one or more sample concentration measurements, such that the variation of sample isotope ratio and concentration can be analysed over time. Additionally or alternatively, the step d) of measuring at least one sample isotope ratio over the measurement time period $t_s^n$ in the spectrometer comprises measuring a plurality of sample isotope ratios over the measurement time period $t_s^n$ in the spectrometer. Then, the step f) of determining the plurality of calibrated isotope ratios and the plurality of sample gas concentration measurements may comprise associating each of the plurality of sample isotope ratios measured over the measurement time period $t_s^n$ with a respective time from the measurement time period $t_s^n$. In this way, multiple isotope ratio measurements taken over a single measurement time period $t_s^n$ can be calibrated and time-referenced and their variation may be analysed, together with the corresponding sample concentration variation over the same time period. In embodiments, the step b) of measuring a sample concentration $c_s^n$ over at least a part of the measurement time period $t_s^n$ may comprise measuring a plurality of sample concentrations, each sample concentration measurement being over a respective (different) part of the measurement time period $t_s^n$.

The duration of each measurement time period $t_s^n$ for $n \geq 1$ may be the same. Alternatively the duration may vary between different measurement time periods $t_s^n$ with n. For example, the duration of a measurement time period $t_s^{n+1}$ that is subsequent to the certain measurement time period $t_s^n$, may be set on the basis of a rate of change of sample concentration $c_s^n$ or a statistic of the sample concentration $c_s^n$) during the certain measurement time period $t_s^n$. In particular, the duration of the subsequent measurement time period $t_s^{n+1}$ (or an increase in the duration over that of the certain measurement time period $t_s^n$) may have an inverse relationship to the rate of change of (statistic of the) sample concentration $c_s^n$ during the certain measurement time period $t_s^n$. In this way, the duration of the subsequent measurement time period $t_s^{n+1}$ may be short (or shortened) if the (statistic of the) sample concentration is changing rapidly, but longer (or lengthened) if the (statistic of the) sample concentration is changing at a slow rate. In some embodiments, the duration of a measurement time period $t_s^n$ may be around one minute.

In the preferred embodiment, the step d) of measuring the isotope ratio of the reference gas at the reference gas concentration $c_{ref}^n$ in the spectrometer does not take place during the measurement time period $t_s^n$. Preferably, this takes place during a reference time period $t_{ref}^n$ that is subsequent to the measurement time period $t_s^n$. This allows the sample concentration information measured during the measurement time period $t_s^n$ to be used when measuring the isotope ratio of the reference gas. The duration of reference time period $t_{ref}^n$ is typically shorter than the duration of the measurement time period $t_s^n$ and usually much shorter (no more than 10%, 20%, 30%, 40% or 50%).

The selected reference gas concentration $c_{ref}^n$ is not necessarily the same as the measured reference gas concentration. Indeed, the difference may be significant. The selected reference gas concentration $c_{ref}^n$ is normally a nominal value. A correction factor (for example, $X_{cor}$) may therefore be determined on the basis of a previous measurement of the reference gas concentration and a comparison between that measurement and the nominal reference gas concentration selected prior to the measurement. This correction factor may then be applied to the measured sample gas concentration $c_s^n$ in order to select the reference gas concentration $c_{ref}^n$ for the next reference time period $t_{ref}^n$ (for example, by making $c_{ref}^n = c_s^n \times X_{cor}$). In one sense, it may be understood that the method further comprises adjusting the reference gas concentration $c_{ref}^n$ (which may be termed a first reference gas concentration) for reference to the sample measured during the measurement time period $t_s^n$ (which may be termed a first measurement time period), on the basis of the measured sample concentration $c_s^n$ during measurement time period $t_s^n$, so as to provide a second reference gas concentration $c_{ref}^{n+1}$, different from the first reference gas concentration, to the spectrometer for use with reference to a second, subsequent measurement time period $t_s^{n+1}$.

The correction may be achieved as follows. Before step a) is carried out, the method advantageously further comprises: selecting a preceding reference gas concentration $c_{ref}^{n-1}$ for use in connection to a time period that is before the measurement time period $t_s^n$. Then, the step c) of selecting a reference gas concentration $c_{ref}^n$ for the spectrometer for reference to the sample measured during the measurement time period $t_s^n$ may be on the basis of the measured sample concentration $c_s^n$ during measurement time period $t_s^n$ and on the basis of the selected preceding reference gas concentration $c_{ref}^{n-1}$. In particular, the method may further comprise measuring the concentration of the reference gas at the selected preceding reference gas concentration $c_{ref}^{n-1}$. For example, the step of measuring the concentration of the reference gas at the selected preceding reference gas concentration $c_{ref}^{n-1}$ may take place during a preceding reference time period $t_{ref}^{n-1}$ that is prior to the measurement time period $t_s^n$. Additionally or alternatively, the method may further comprise calculating a correction factor based upon a ratio of the selected preceding reference gas concentration $c_{ref}^{n-1}$ to the measurement of the preceding reference gas concentration. Then, the step c) of selecting the reference gas concentration $c_{ref}^n$ may comprise applying the calculated correction factor to the sample concentration $c_s^n$ measured over the at least part of the measurement time period $t_s^n$. In the preferred embodiment, wherein the step of selecting a preceding reference gas concentration $c_{ref}^{n-1}$ (especially where n=1, such that n−1=0) is on the basis of an anticipated sample concentration for the said measurement time period. Thus, there may be a preceding reference time period $t_{ref}^n$, during which the step of measuring the concentration of the reference gas at the selected preceding reference gas concentration $c_{ref}^0$ is carried out. This preceding reference time period $t_{ref}^0$ may not be subsequent to any measurement time period $t_s^n$, but it may precede a first measurement time period $t_s^1$. Since no information about the sample concentration may be available at this preceding reference time period $t_{ref}^0$, the preceding reference gas concentration $c_{ref}^0$ is selected by estimation, approximation or use of a nominal value for the sample concentration $c_s^1$ during the first measurement time period $t_s^1$.

The step b) of measuring the sample concentration $c_s^n$ over at least a part of the measurement time period $t_s^n$ can be achieved in different ways. In some embodiments, the step b) comprises determining a (time-based) statistical characteristic of the sample concentration over the at least part of the measurement time period $t_s^n$, in particular an average of the sample concentration over the at least part of the measurement time period $t_s^n$. The average may be a mean, median or mode, but other statistical characteristics of the measurement data may be used. Then, the step e) of calibrating the isotope ratio of the sample uses the measured isotope ratio of the reference gas at the determined statistical characteristic of the sample concentration or average sample concentration.

Additionally or alternatively, the step b) of measuring the sample concentration $c_s^n$ over at least a part of the measurement time period $t_s^n$ can take place at different times. For example, the at least part of the measurement time period $t_s^n$ may be the whole of the measurement time period $t_s^n$. This may especially be used when the measured sample concentration $c_s^n$ is an average of the sample concentration over the measurement time period $t_s^n$. In other embodiments, the at least part of the measurement time period $t_s^n$ is only a last part of the measurement time period $t_s^n$. For example, this may be only a portion of the measurement time period $t_s^n$.

The step e) of calibrating the at least one isotope ratio of the sample measured during the measurement time period $t_s^n$ uses the measured isotope ratio of the reference gas at the measurement reference gas concentration $c_{ref}^n$, but this calibration may also use other parameters. For example, the calibration may use a measured isotope ratio of the reference gas at the preceding reference gas concentration $c_{ref}^{n-1}$, measured during a preceding reference time period $t_{ref}^{n-1}$. In the preferred embodiment, the method further comprises measuring the isotope ratio of the reference gas at a preceding reference gas concentration $c_{ref}^{n-1}$ in the spectrometer during a preceding reference time period $t_{ref}^{n-1}$ that is before the measurement time period $t_s^n$ (n>1). Then, the step e) of calibrating the at least one isotope ratio of the sample measured during the measurement time period $t_s^n$ preferably uses the measured isotope ratio of the reference gas at the preceding reference gas concentration $c_{ref}^{n-1}$ and the measured isotope ratio of the reference gas at the measurement reference gas concentration $c_{ref}^n$.

Although some embodiments may only measure a single sample isotope ratio over the measurement time period $t_s^n$ in the spectrometer, other embodiments may measure a plurality of sample isotope ratios over the measurement time period $t_s^n$ in the spectrometer. In other words, the step d) of measuring at least one sample isotope ratio over the measurement time period $t_s^n$ in the spectrometer may comprise measuring a plurality of sample isotope ratios over the measurement time period $t_s^n$ in the spectrometer. This is advantageously used in conjunction with the use of the measured isotope ratio of the reference gas at the preceding reference gas concentration $c_{ref}^{n-1}$ in the calibration, as discussed above, but that is not necessarily always the case. Either way, the step e) of calibrating the at least one isotope ratio of the sample measured during the measurement time period $t_s^n$ may comprise, for each of the plurality of sample isotope ratios: identifying a respective sample characteristic for the respective sample isotope ratio; determining a respective isotope ratio of the reference gas for the identified respective sample characteristic; and calibrating the respective sample isotope ratio using the determined respective isotope ratio of the reference gas. The respective sample characteristic for the respective sample isotope ratio may comprise one or both of: a respective sample concentration for the respective sample isotope ratio; and a respective sample measurement time for the respective sample isotope ratio. An interpolation between two isotope ratio measurements of the reference gas may be used to increase the range of variation in sample concentration that may be analysed at a specific minimum level of accuracy.

The step of identifying a respective sample characteristic for the respective sample isotope ratio may comprise measuring the respective sample concentration for the respective sample isotope ratio. Where the measured isotope ratio of the reference gas at the preceding reference gas concentration $c_{ref}^{n-1}$ is used in the calibration, the step of determining a respective isotope ratio of the reference gas for the identified respective sample concentration beneficially comprises interpolating between the measured isotope ratio of the reference gas at the preceding reference gas concentration $c_{ref}^{n-1}$ and the measured isotope ratio of the reference gas at the measurement reference gas concentration $c_{ref}^n$. This may be a linear or non-linear interpolation.

Additionally or alternatively, the step of identifying a respective sample characteristic for the respective sample isotope ratio may comprise measuring the respective sample measurement time for the respective sample isotope ratio. Where the measured isotope ratio of the reference gas at the preceding reference time period $t_{ref}^{n-1}$ is used in the calibration, the step of determining a respective isotope ratio of the reference gas for the identified respective sample concentration beneficially comprises interpolating between the measured isotope ratio of the reference gas at the preceding reference time period $t_{ref}^{n-1}$ and the measured isotope ratio of the reference gas at the measurement reference time period $t_{ref}^n$.

In the preferred embodiment, the continuous sample is derived from one or more of: ambient air; an open air source; a plant chamber; and a gas monitoring input. In many of these cases, a large-scale long-term variation in sample concentration may be possible. For instance, the sample measurement time period may be around one minute, but samples may be received continuously for one week or multiple weeks. The sample preferably comprises $CO_2$. The reference gas advantageously comprises at least one identical species to the sample gas.

In another aspect, the present invention provides a computer program configured when operated by a processor to carry out the method as described herein.

In a further aspect, there is provided a controller for a continuous sample isotope ratio spectrometer, configured to control the isotope ratio spectrometer to operate in accordance with the method as described herein. Optionally, there is provided an isotope ratio spectrometer configured to receive a continuous sample and comprising such a controller.

Various preferred features of the present invention will be apparent from the appended claims and from the following specific description of some preferred embodiments.

BRIEF DESCRIPTION OF THE DRAWINGS

The invention may be put into practice in a number of ways and some embodiments will now be described by way of example only and with reference to the accompanying figures in which.

DETAILED DESCRIPTION OF PREFERRED EMBODIMENTS

Figure 1:
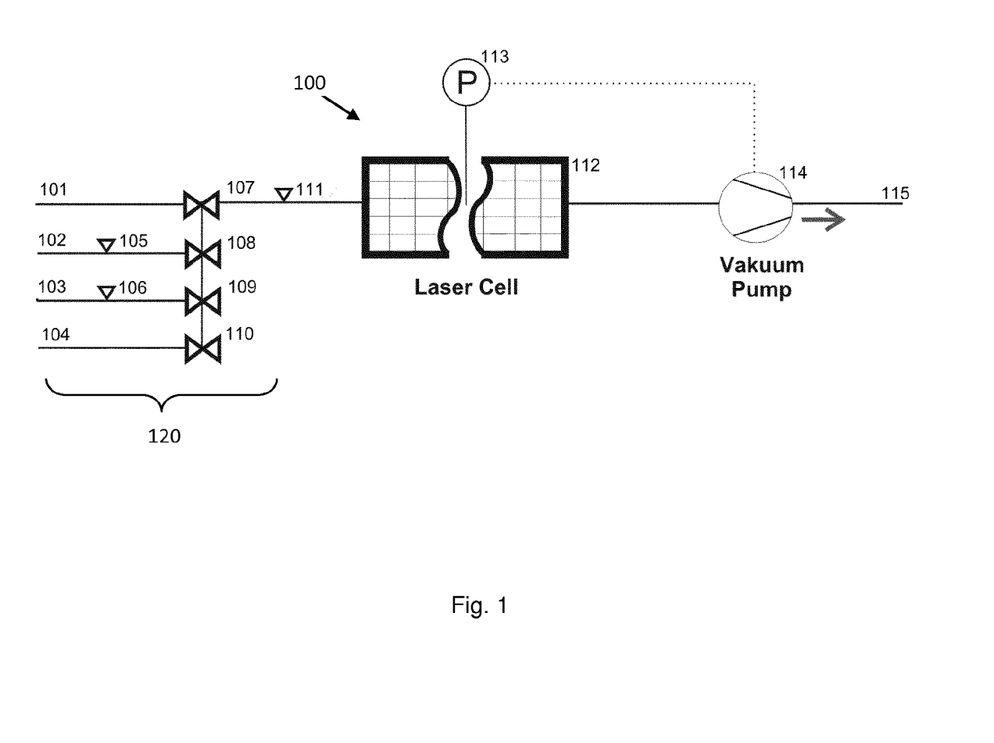
FIG. 1 shows a schematic layout of an isotope ratio optical spectrometer interfaced to a gas inlet system in accordance with an existing design.

Referring to FIG. 1, there is shown schematically an isotope ratio optical spectrometer 100 interfaced to a multi-port inlet system 120 which represents one particularly preferred arrangement for implementation of the method embodying the present invention. Whilst the isotope ratio spectrometer described below is an optical spectrometer, it will be appreciated that an isotope ratio mass spectrometer could equally be employed. The arrangement shown in FIG. 1 is shown and explained in more detail in our co-pending application numbers GB1306806.9, GB1306807.7 and GB1306808.5, the contents of which are incorporated by reference.

The optical spectrometer is a laser spectrometer. A sample (or reference) gas to be measured is transported from the multi-port inlet system 120 through a multi-pass measurement cell 112 in the laser spectrometer by a vacuum pump 114, such as a membrane pump, in the outlet 115 from the spectrometer that pumps the cell. The measurement cell has a total optical path length of approximately 5.4 m. The incoming gas is directly and completely transferred into the measurement cell 112. A filter (not shown) upstream of the cell prevents transfer of particles into the cell. The inlet flow into the measurement cell in this embodiment is limited by a fixed flow restriction 111 and is set to allow a gas flow rate of 80 ml/min into the cell for atmospheric pressure at the inlet ports 101, 104 and 0.5 bar(g) at inlet ports 102, 103. The actual flow through the measurement cell however depends on the pressure of the delivered gas. The pressure in the measurement cell 112 is kept constant by controlling the pump speed, for example in this embodiment by feedback to the pump 114 of signals generated from a pressure gauge 113 connected to the cell 112. It is also possible in other embodiments to have an adjustable valve between cell 112 and pump 114 and to control the valve instead of the pump 114, e.g. using the feedback from the pressure gauge 113. In this way, the pressure in the cell is desirably maintained generally in the range 20-200 mbar(a) or preferably 40-200 mbar(a) or more preferably 40-150 mbar(a). The pressure in the measurement cell is typically kept constant at approximately 100 mbar(a) (or in the range 20 to 150 mbar(a), or even to 200 mbar(a)). The operating measurement range of the cell is 200-4,000, preferably 200-3,500, ppm of $CO_2$ in air or in $N_2$ with highest performance of detection between 200-1,500 ppm, especially 300-1,500 ppm of $CO_2$.

On the gas inlet line into the measurement cell, a multi-port valve (shown schematically as distinct valves 107-110 for illustration purposes) allows switching between four different gas inlet ports 101-104. One of these ports 101 is connected to a gas inlet and referencing system as described in more detail below (see FIG. 2). The remaining ports 102-104 can optionally be used, for example, for additional sample gas (e.g. ambient air at port 104) and/or calibration gases for additional concentration calibration 102, 103. The latter requires one or two references with known concentration. The inlet and referencing system connected to port 101 is typically used for calibration of the concentration dependence of the isotope ratio measurement and for the isotope ratio dependence of the isotope ratio measurement, which forms the method that embodies the present invention and which is described below.

Figure 2:
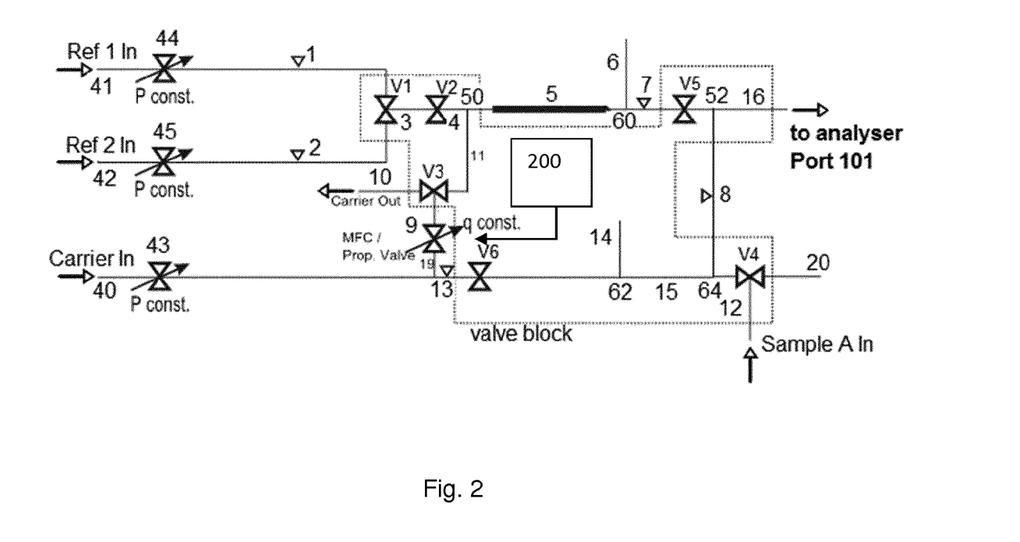
FIG. 2 shows a schematic layout of a gas inlet and referencing system in accordance with an existing design.

For linearity calibration and delta scale contraction, mixtures of reference $CO_2$ with carrier gas, using $CO_2$ from two different sources (with different known isotope ratios), are required. The arrangement of FIG. 2 shows a gas inlet that provides a convenient way to supply these different concentration gases to the spectrometer by mixing pure $CO_2$ with $CO_2$-free air (also termed zero air), or other $CO_2$-free gas. The dilution is performed to give the required 200-4,000 (preferably 200-3,500) ppm $CO_2$ in air (or in $N_2$). Further advantageously, $CO_2$-free air can either be produced in the field using a $CO_2$ absorber or delivered in gas tanks.

The gas inlet system of FIG. 2 provides a better stability of the gas flow and avoids possible isotope fractionation by a flow controller. The flow of $CO_2$-free air (zero air) is controlled by a flow control means (e.g. flow controller or a proportional valve) and instead the $CO_2$ flow is kept constant. For higher dynamic range and flow matching the dilution may be carried out in two steps.

Referring to FIG. 2, there is shown a gas inlet and referencing system suitable for implementing the method embodying the present invention. Firstly, it is noted how the system connects with the spectrometer shown in FIG. 1. The exit line 16 of the system shown in FIG. 2 connects with port 101 of the gas inlet system shown in FIG. 1. Thus, gases exiting from the system shown in FIG. 2 enter the spectrometer shown in FIG. 1 for isotope ratio measurement. The system is configured to be able to deliver sample gas and reference gas to the optical laser spectrometer.

Supplies of two pure $CO_2$ reference gases (ref 1 and ref 2) are provided 41, 42. The isotope ratio ($^{13}C/^{12}C$ and/or $^{18}O/^{16}O$) of each $CO_2$ supply is known. The flow of each supply of $CO_2$ is controlled by a respective valve 44, 45, which are constant pressure valves, and a respective flow restriction 1, 2 on the supply lines. The two valves V1 and V2 3, 4 on the reference gas line allow switching between the two reference gases as well as shutting them both off from the rest of the system to save reference gas. A supply of a carrier gas, which is $CO_2$-free air, is also provided 40, the flow of which is controlled by a respective valve 43, which is a constant pressure valve. For simplicity, FIG. 3 shows the flow scheme of the referencing section of the inlet system alone.

To avoid fractionation of the $CO_2$, a constant flow of $CO_2$ of 400 µl/s (24 ml/min) from a selected one of the $CO_2$ reference supplies is mixed into a variable flow of $CO_2$-free air (or other carrier gas) (flow rate 3 to 100 ml/min) using a mass flow controller or a proportional valve 9 on the carrier gas line. The mass flow controller or a proportional valve 9 is in this embodiment computer controlled (preferably, most or all valves shown in the system of the invention are computer controlled). That is, the $CO_2$ is not subject to variable mass flow control, thus avoiding fractionation, but rather it is the $CO_2$-free air that is dynamically flow controlled. The gases first mix at T-junction 50, which is a first mixing junction. The gases further mix downstream inside a mixing zone 5, which is a tube that provides an homogeneous mixture of the two gases. The flow restrictions 1, 2 and constant input pressure valves 44, 45 of the $CO_2$ references define the constant $CO_2$ flow into the mixing zone 5. The $CO_2$ concentration of this resultant pre-mixture is designed to be in the range from 4,000 ppm to 13,000 ppm. The mixing zone 5 is necessary to ensure that the $CO_2$ and the zero air are thoroughly mixed. As the flow rate here can be larger than 100 ml/min, the residence time of the gas in the mixing zone 5 may be very short.

Figure 3:
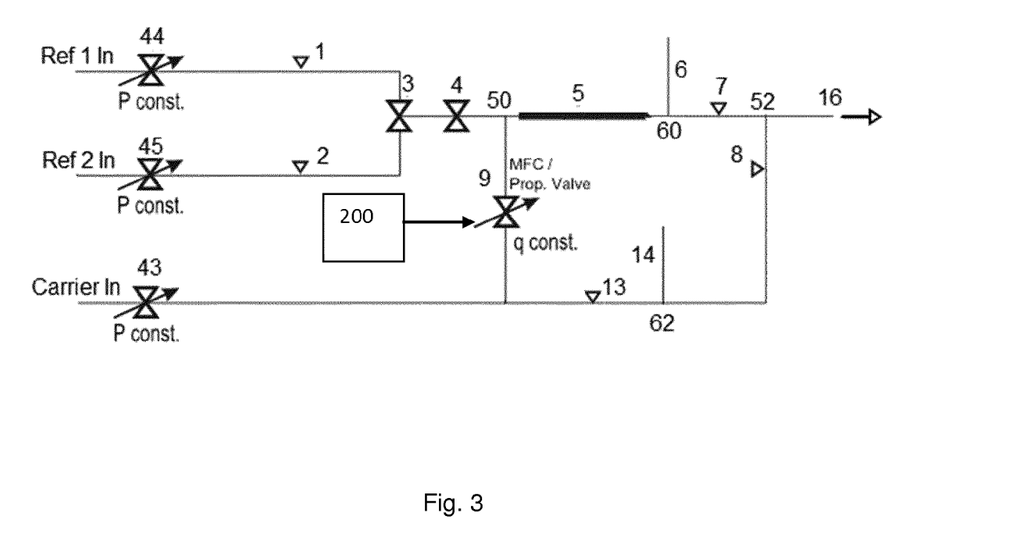
FIG. 3 shows a schematic layout of the referencing section of the system shown in FIG. 2.

Co-pending application numbers GB1306806.9, GB1306807.7 and GB1306808.5 set out some preferred parameters and diameters for the components and flow rates in the arrangements of FIGS. 2 and 3.

Still referring to FIGS. 2 and 3, the $CO_2$ pre-mixture is further mixed with more $CO_2$-free air (carrier gas) at a second T-junction or flow splitter 52. This is thus a second mixing junction. A second dilution of the reference flows is set to an appropriate fixed ratio (for example 1:30). The flow to the second mixing T-junction is defined by two flow restrictions 7, 8, which in this embodiment ensure a ratio between the pre-mixture and CO2-free air of 1:30. That is, flow restriction 7 restricts flow of pre-mixture and flow restriction 8 restricts flow of carrier gas. The flow of the pre-mixture is defined by the flow controller 9 and is always higher than 1/30 of the gas flow into the laser spectrometer. This two stage dilution is preferable due to limitations of the dynamic range of down-mixing in practice. The progressive linearity calibration of the concentration dependence is then performed by use of flow controller 9.

The input pressure of both restrictions 7 and 8 is kept equal at approximately atmospheric pressure by two openings in the form of open tubes or capillaries 6, 14 on the pre-mixture exit line and the carrier gas line respectively. Thus, the rest of the pre-mixture is blown out of the opening 6 positioned after (downstream of) the mixing zone, between the mixing zone 5 and the flow restriction 7. The flow of the CO2-free air towards the second mixing split is defined by a flow restriction 13 and the constant pressure in the supply 43 of the $CO_2$-free air. The gas flow at the restriction 13 is always higher than the gas flow to the laser spectrometer. The differential amount of $CO_2$-free air carrier gas is blown out of an opening 14 on the carrier gas line.

The openings 6, 14 are situated on T (or Y) piece connections 60, 62. The openings 6, 14 are dimensioned such that the gas velocity is always higher than the diffusion velocity of $CO_2$ in air to avoid contaminations of the reference gases. From the above it can be seen that the reference gas flows are very low and should not be dynamically regulated or actively controlled (i.e. valves 1 and 2 (at locations 3, 4) are typically on/off valves). Thus, the reference gas flows from the reference gas supplies, via valves 1 and 2, are not changed when changing the $CO_2$ concentration in the spectrometer. Instead, a first dilution of the reference gas flow is dynamically regulated by controlling flow of the zero air (using computer controlled valve 9 controlled by processor 200).

The referencing system is designed to allow dilution of the supplied gases by mixing different gases with each other to change concentrations of the desired gas species (e.g. $CO_2$ in zero air). It can be seen that by varying the flow of the carrier gas using mass flow controller (9), the concentration of $CO_2$ reference gas in the $CO_2$-free carrier gas can be varied. The referencing system allows any concentration of the $CO_2$ for linearity calibration in the measurement range of the spectrometer from 100-4,000 ppm, more preferably 200-3,500 ppm. In this way, isotope ratio measurements can be taken in the spectrometer at a plurality of different $CO_2$ concentrations to enable a concentration dependence of the isotope ratio measurement to be determined in accordance with the method of the present invention.

An exit line 16 takes the flow from the mixing zone into the optical laser spectrometer after the second stage of dilution. The output flow into the optical laser spectrometer is defined by the spectrometer itself and is ideally 80 ml/min. The pressure at the outlet 16 that interfaces to the spectrometer is designed to be around atmospheric pressure.

Reference gas switching is also possible with the arrangement of FIGS. 2 and 3, and further details may again be found in GB1306806.9, GB1306807.7 and GB1306808.5.

In addition to the referencing system described above, the gas inlet system shown in FIG. 2 further comprises a sample inlet system for introducing a sample gas (i.e. of unknown isotope ratio and/or concentration) into the spectrometer. The details of this are not critical to the present invention and in any event may be found in GB1306806.9, GB1306807.7 and GB1306808.5. In brief, however, a flow of $CO_2$-free air is mixed with a $CO_2$ sample flow coming from a sample inlet port 12 (FIG. 2) to which is connected a supply of sample gas ($CO_2$). In this embodiment, the supply of $CO_2$-free air for the sample flow is the same supply 40 as used for dilution of the reference gases in the referencing system.

Samples are frequently only available in minute quantities. Thus, the sample inlet system must ensure that little or no sample is lost. The preferred sample inlet system ensures 100% sample transfer from the sample input port to the laser spectrometer 16. A constant flow to the laser spectrometer is ensured by filling the differential volume between the sample flow and the flow to the laser spectrometer with a carrier or dilution gas, which in this case is $CO_2$-free air (zero air). No sample is wasted and the concentration of $CO_2$ in the gas flow to the laser spectrometer is kept constant and in the optimal range.

Having described a preferred arrangement for the supply of sample gas and reference gas or gases to the spectrometer at a controllable concentration, the method embodying the present invention will now be described with reference to the flow chart of FIG. 4 and to the plot of gas concentration against time in FIG. 5.

Figure 4A:
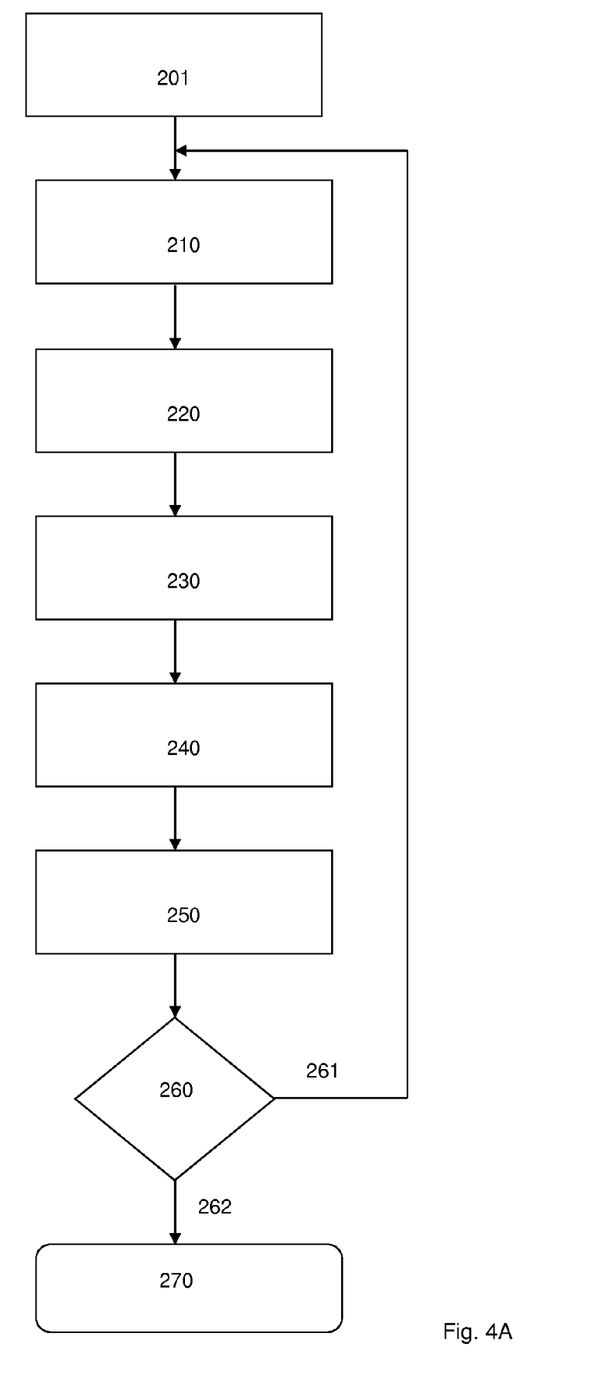
FIG. 4A shows a flowchart of a process for measuring reference gas and sample gas isotope ratios and concentrations, that embodies the present invention.

Referring to FIG. 4a, there is shown a flowchart of a process for measuring reference gas and sample gas isotope ratios and concentrations. A first reference gas measurement step 301 is optional. In this step, a reference gas concentration is selected arbitrarily. For example, it may be selected on the basis of an anticipated sample concentration for the sample to be measured in a subsequent step. The concentration of the reference gas at the selected initial concentration is measured, preferably by taking a spectroscopy measurement of the reference gas nominally supplied at the selected concentration.

Then, a correction factor is calculated based upon a ratio of the selected (nominal) reference gas concentration to the concentration of the reference gas that has just been measured. This correction factor can be used subsequently. This initial reference gas measurement step 201 can be considered a $0^{th}$ time period, because it precedes a first measurement of the sample.

In a first sample measurement step 210, at least one sample isotope ratio is measured over a measurement time period using the spectrometer. Typically, multiple isotope ratios are measured for the sample. As explained above, the sample concentration can vary over this time period. The first sample measurement step 210 marks the start of an $n^{th}$ cycle, with n=1, 2, . . . , N.

In a second sample measurement step 220, a concentration of the sample is measured. Although the first sample measurement step 210 and second sample measurement step 220 are shown as concurrent steps, they normally take place in parallel and the duration of these two steps can be represented as an $n^{th}$ measurement time period. As will be discussed below, the sample concentration measurement can take place simultaneously with the isotope ratio measurement. Alternatively, the sample concentration measurement may take place during a part of the time period during which the sample isotope ratio is being measured, particularly a latter part of that time period.

Subsequently, a reference gas concentration selection step 330 is performed. A new reference gas concentration is selected based on the measured sample concentration. Moreover, the reference gas concentration that is selected can be based on the calibration factor that was determined in initial reference gas measurement step 201. An example of this will be shown below.

In reference gas isotope ratio measurement step 240, the spectrometer is used to measure the isotope ratio of the reference gas at the selected concentration. This take place during a $n^{th}$ reference time period, n=1, 2, . . . , N. This isotope ratio measurement can be used to identify a calibration factor for the sample isotope ratio measurement at that concentration. In calibration step 250, the at least one isotope ratio of the sample is calibrated using the measured isotope ratio of the reference gas at the corresponding selected reference gas concentration.

Preferably, decision step 260 takes place next. If there is a further sample to be analysed, route 261 is taken and the process returns to the first sample isotope ratio measurement and continues on from there, with n=n+1. However, during the repeated process, the correction factor used in the selection of the reference gas concentration (in reference gas concentration selection step 230) may be taken from the measurement of the reference gas in reference gas measurement step 250 (that is, during the $(n-1)^{th}$ reference time period. Optionally, the concentration of the reference gas is also measured during this step and a new correction factor is determined.

However, if decision step 260 determines that no further samples are to be analysed (that is n=N), the process proceeds along route 262 terminating step 370, where the process ends.

Figure 4B:
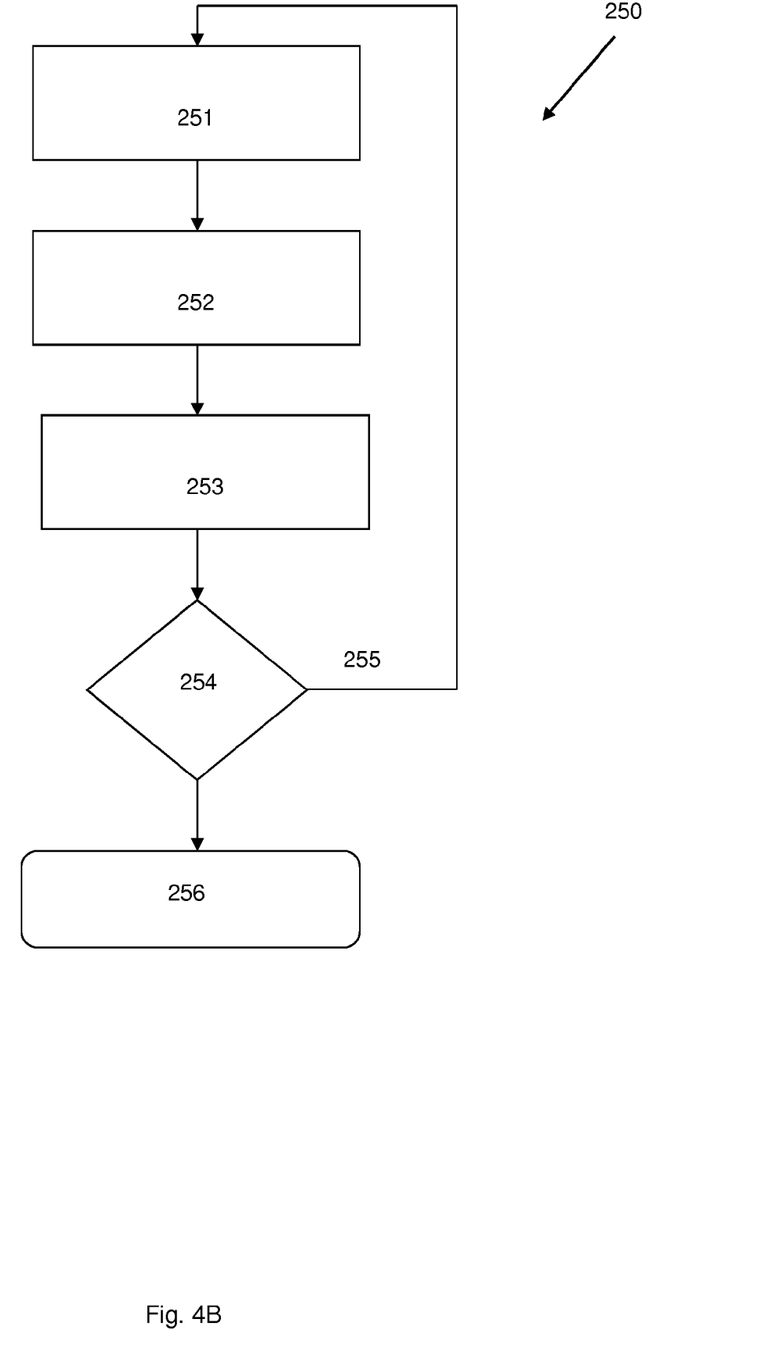
FIG. 4B shows a flowchart of an optional part of the process shown in FIG. 4A, for calibrating sample gas isotope ratios.

Referring next to FIG. 4b, there is shown a flowchart of an optional part of the process shown in FIG. 4a, for calibrating sample gas isotope ratios. This is an optional technique for carrying out the calibration step 250, in cases where multiple isotope ratio measurements are taken in first sample measurement step 210.

In sample concentration identification step 251, a sample concentration is identified for the first isotope ratio measurement of the sample taken in first sample measurement step 210. Next, an isotope ratio of the reference gas is determined for the identified sample concentration in step 251. This takes place in isotope ratio determination step 252. Then, the sample isotope ratio measurement is calibrated using the determined reference gas isotope ratio from determination step 252. This takes place in calibration step 253.

In measurement decision step 254, the decision is made as to whether this is the final isotope ratio measurement for the sample that was taken in first measurement step 210. If not, route 255 is taken and the process returns to sample concentration identification step 251. Steps 251, 252, 253 and 254 are then repeated for the next sample isotope ratio measurement that was taken in first sample measurement step 210. If all of the sample isotope ratio measurements have been processed, decision step 254 proceeds to terminating step 256 and the process returns to decision step 260 shown on FIG. 4a.

The process shown in FIG. 4b may be especially useful where an interpolation can be carried out in order to determine the reference gas isotope ratio for a concentration of the reference gas that was not measured. This will be explained below, with reference to a "bracketing" approach.

Figure 5:
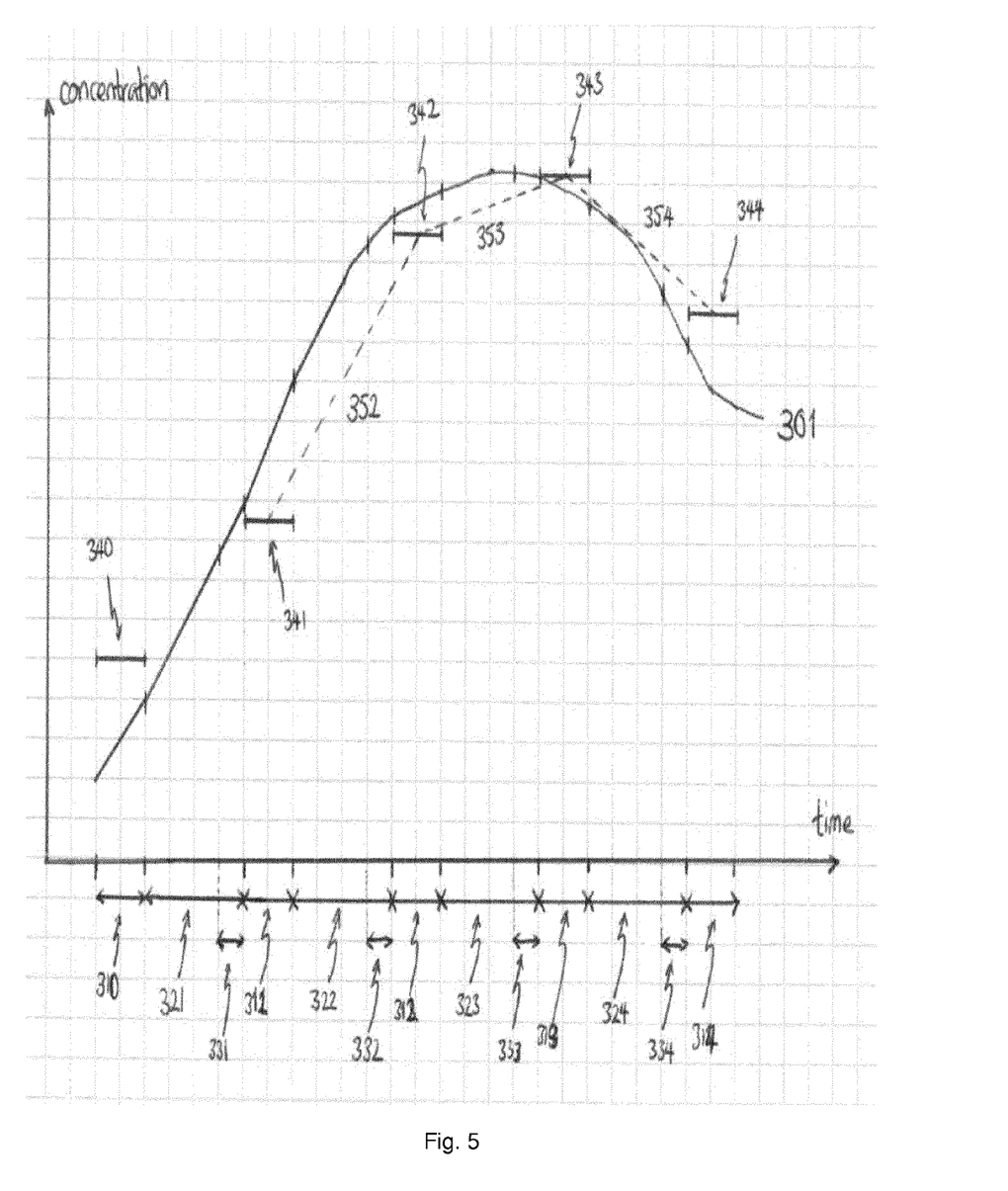
FIG. 5 shows a plot of an example gas concentration for each of a reference gas and a sample gas against time, showing when respective isotope ratios are measured.

Referring next to FIG. 5, there is shown a plot of an example gas concentration for each of a reference gas and a sample gas against time, showing when respective isotope ratios are measured. The variation of the sample concentration over time 301 is shown as the main plot (illustrating a typical concentration trend during a measurement). This time period is divided into a series of time durations, during which the spectrometer is used for a different measurements, as will be discussed below.

In this mode, the sample (for example, ambient air). and reference (or working standard) gases are measured alternately. In an initial reference time period 310, the reference gas is measured at a default concentration 340 (which can be set by the user). A first measurement time period 321 follows (typically a few minutes). During this first measurement time period 321, the sample is measured to determine at least one isotope ratio. As can be seen, the sample concentration changes (here, increases) during the first measurement time period 321. During a portion 331 of the first measurement time period 321, the sample is measured to determine the concentration of the sample. This is typically an average concentration over the portion 331 and the length (or start and finish times) of the portion 331 is adjustable. Normally, the portion 331 is at the end of the first measurement time period 321.

The reference gas is now measured during a first reference time period 311 at the concentration measured during the portion 331 of the first measurement time period 321. This reference gas concentration 341 is shown and an isotope ratio measurement for the reference gas is taken.

In the next step, second measurement time period 322, the sample is measured again, with at least one isotope ratio measurement being made during this period and a concentration measurement being made during a portion 332 of the second measurement time period 322. Subsequently, a second reference time period 312 takes place and an isotope ratio for the reference gas is measured at the concentration determined during the portion 332 of the second measurement time period 322. Again, the reference gas concentration 342 is shown.

Although at least one isotope ratio measurement (and preferably multiple measurements) were made during the second measurement time period 322, these are desirably calibrated against the reference gas isotope ratio measurements. This can be achieved by taking a linear interpolation 352 of the two neighbouring reference gas isotope ratio measurements 341 and 342. Each individual data point (isotope ratio) of the sample measurement (on basis of the integration time) during the second measurement time period 322 is referenced against the isotope ratio determined from the linear interpolation 352. At each data point, a quasi-reference is available at a matched concentration without any dilution of the sample. Thus, the sample concentration is not lost using this referencing technique and a more accurate calibration of the at least one sample isotope ratio measurement can be made.

This is repeated during a third measurement time period 323, with at least one isotope ratio measurement being made during this period and a concentration measurement being made during a portion 333 of the third measurement time period 323. Then, a third reference time period 313 takes place and an isotope ratio for the reference gas is measured at the concentration determined during the portion 333 of the third measurement time period 323 (reference gas concentration 343 is shown once more). Again, a linear interpolation 353 between the second reference gas concentration 342 and third reference gas concentration 343 is shown, which can be used for calibration of the data points measured during the third measurement time period 323.

Finally, a fourth measurement time period 324 is shown, with at least one isotope ratio measurement being made during this period and a concentration measurement being made during a portion 334 of the fourth measurement time period 324. During a fourth reference time period 314, an isotope ratio for the reference gas is measured at the concentration determined during the portion 334 of the fourth measurement time period 324 (as shown by reference gas concentration 344). Another linear interpolation 354 between the third reference gas concentration 343 and fourth reference gas concentration 344 is used for calibration of the data points measured during the fourth measurement time period 324.

For some applications (such as multiple input ports at different concentration levels), the linear interpolation technique may not be used. In this case, the concentration of the reference measured during each reference time period 311, 312, 313, 314 matches the average of the sample concentration over the whole sample measurement time. In other words, the portion 331, 332, 333, 334, becomes essentially 100% of the respective measurement time period 321, 322, 323, 324. The isotope ratio of the sample is calibrated using only the isotope ratio measurement of the reference as measured at the determined concentration (known as post-referencing or non-bracketing technique). Nonetheless, the reference concentration is matched to the sample concentration as measured.

Calibration of the concentration measurements and internal calibrations are also carried out. The flow controller is calibrated once after connecting a working standard. To avoid multiple calibrations over a wide range the system self-calibrates during measurements.

As discussed above, to match sample and working standard concentrations, the uncalibrated raw values for the concentration from the instrument are matched. Therefore a desirable requirement for the self-calibration is that the measured raw concentration of a working standard matches the set value for the same working standard. Each time a working standard is measured, a correction factor is updated on basis of the uncalibrated raw values of the sensor. For the next reference the factor with the latest update is applied. For instance (using the example illustrated above with reference to FIG. 5), the concentration of the reference gas is also measured during the initial reference time period 310 and this is compared with the concentration that was initially selected. A correction factor is determined based on the ratio of the selected (nominal) reference concentration to the measured reference concentration. Then, this correction factor is used subsequently in the selection of the first reference concentration to be used the first reference time period 311. This will be illustrated with an example below. Matching intensities for the reference intensity to that measured for the sample may alternatively be effective.

This example shows a workflow with fictive sample concentration and the behavior of the reference concentration, when using the approach outline above. In the beginning, the example shows a bad match of set value for the working standard concentration with the measured concentration of the working standard. By the use of the self-learning calibration technique proposed above, the reference concentration value is cause to approach the final sample concentration value. As can be seen, the correction factor is iteratively improved by each sample and reference concentration measurement.

| Index | Label | Port | Concentration | Measured Concentration | C_corr |
|---|---|---|---|---|---|
| | | | | | 1 |
| 1 | Reference | Ref Port 1 | 380.0 | 392.0 | 0.969 |
| 2 | Sample | Sample B | | 480.0 | |
| 3 | Reference | Ref Port 1 | 465.3 | 477.3 | 0.975 |
| 4 | Sample | Sample B | | 480.0 | |
| 5 | Reference | Ref Port 1 | 467.9 | 479.9 | 0.975 |
| 6 | Sample | Sample B | | 485.0 | |
| 7 | Reference | Ref Port 1 | 472.9 | 484.9 | 0.975 |
| 8 | Sample | Sample B | | 490.0 | |
| 9 | Reference | Ref Port 1 | 477.9 | 489.9 | 0.976 |
| 10 | Sample | Sample B | | 495.0 | |
| 11 | Reference | Ref Port 1 | 482.9 | 494.9 | 0.976 |
| 12 | Sample | Sample B | | 470.0 | |
| 13 | Reference | Ref Port 1 | 458.6 | 470.6 | 0.975 |
| 14 | Sample | Sample B | | 471.0 | |
| 15 | Reference | Ref Port 1 | 459.0 | 471.0 | 0.975 |
| 16 | Sample | Sample B | | 474.0 | |
| 17 | Reference | Ref Port 1 | 461.9 | 473.9 | 0.975 |

In index 1, the first reference is measured at default concentration or a user estimate. The set value of the reference gas concentration is 380 ppm and the measured value of this example is 392 ppm. Therefore, a correction factor of 0.969 is calculated. Index 2 shows the first sample measurement with a measured concentration of 480 ppm. In index 3, the set point of the concentration is set to the concentration of the last sample, by applying the correction factor 480 ppm*0.969=465.3 ppm. The correction factor is updated on each reference measurement. To calculate the reference concentration the concentration from the last sample measurement is used together with the last correction factor.

A second example is now shown, in which more than one sample is measured. The reference gas concentration is reference to sample B. Again, the correction factor is iteratively adjusted based on the measurements taken.

| Index | Label | Port | Concentration | Measured Concentration | C_corr |
|---|---|---|---|---|---|
| | | | | | 1 |
| 1 | Reference | Ref Port 1 | 380.0 | 392.0 | 0.969 |
| 2 | Sample In | Sample A | | 512.0 | |
| 3 | Sample Out | Sample B | | 480.0 | |
| 4 | Reference | Ref Port 1 | 465.3 | 477.3 | 0.975 |
| 5 | Sample In | Sample A | | 512.0 | |
| 6 | Sample Out | Sample B | | 480.0 | |
| 7 | Reference | Ref Port 1 | 467.9 | 479.9 | 0.975 |
| 8 | Sample In | Sample A | | 512.0 | |
| 9 | Sample Out | Sample B | | 485.0 | |
| 10 | Reference | Ref Port 1 | 472.9 | 484.9 | 0.975 |
| 11 | Sample In | Sample A | | 512.0 | |
| 12 | Sample Out | Sample B | | 490.0 | |
| 13 | Reference | Ref Port 1 | 477.9 | 489.9 | 0.976 |
| 14 | Sample In | Sample A | | 512.0 | |
| 15 | Sample Out | Sample B | | 495.0 | |
| 16 | Reference | Ref Port 1 | 482.9 | 494.9 | 0.976 |
| 17 | Sample In | Sample A | | 512.0 | |
| 18 | Sample Out | Sample B | | 470.0 | |
| 19 | Reference | Ref Port 1 | 458.6 | 470.6 | 0.975 |
| 20 | Sample In | Sample A | | 512.0 | |
| 21 | Sample Out | Sample B | | 471.0 | |
| 22 | Reference | Ref Port 1 | 459.0 | 471.0 | 0.975 |
| 23 | Sample In | Sample A | | 512.0 | |
| 24 | Sample Out | Sample B | | 474.0 | |
| 25 | Reference | Ref Port 1 | 461.9 | 473.9 | 0.975 |

Figure 6A:
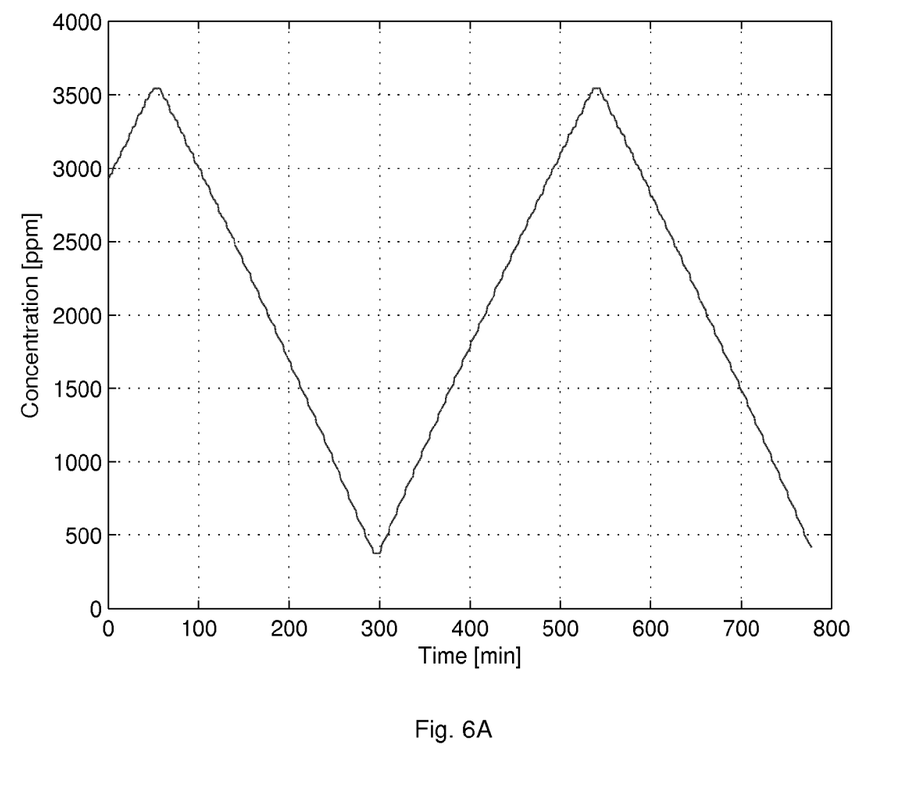
FIG. 6A shows a plot of an example gas concentration for a sample gas against time.

Referring now to FIG. 6A, there is shown a plot of an example gas concentration for a sample gas against time. It can be seen that the sample gas concentration varies significantly.

Figure 6B:
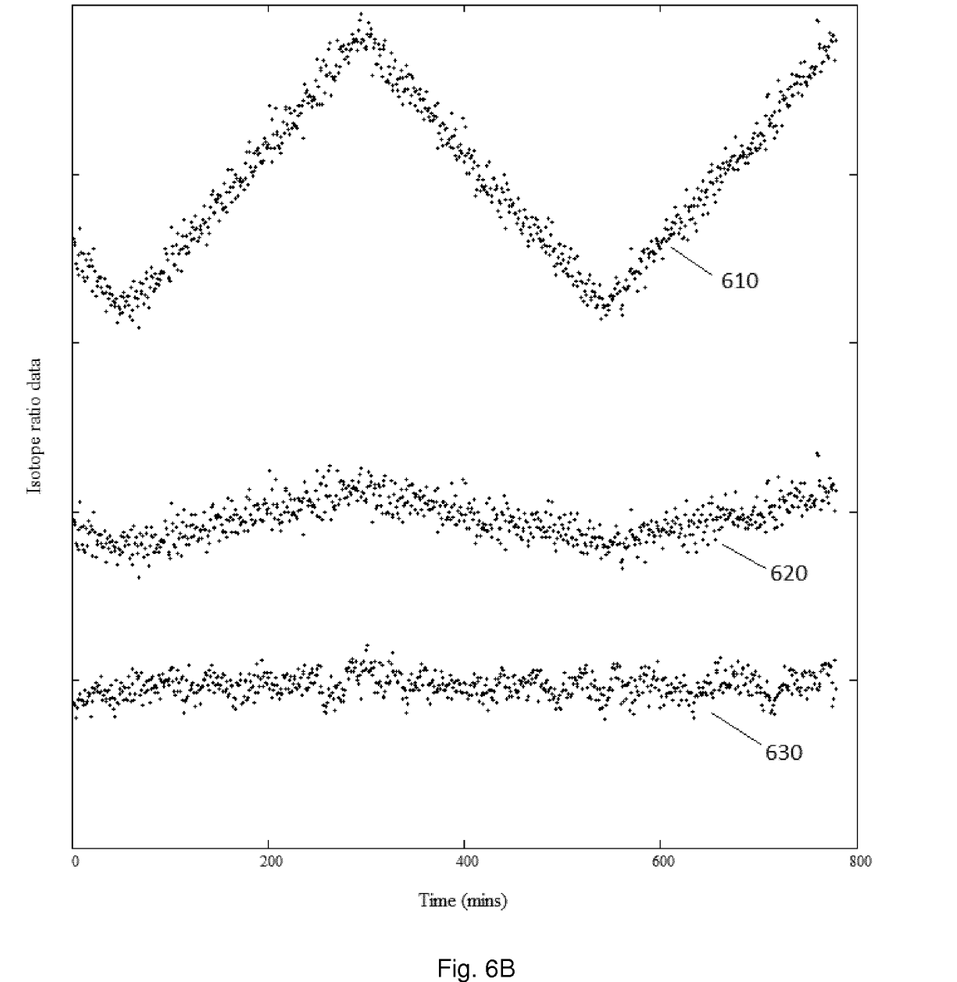
FIG. 6B shows a plot of example isotope ratio deltas for a sample gas, showing raw instrument values, calibrated values using a first embodiment of the invention and calibrated values using a second embodiment of the invention, for the reference gas concentration of FIG. 6A.

Referring next to FIG. 6B, there is shown a plot of example isotope ratio deltas ($\delta_{13C}$) for a sample gas, showing: raw instrument values 610; first calibrated values 620, using the isotope ratio measurements taken for the reference gas with a concentration matched to that of the sample gas shown in FIG. 6A; and second calibrated values 630, using the isotope ratio measurements taken for the reference gas with a concentration matched to that of the sample gas shown in FIG. 6A and linear interpolation, as discussed above. Isotope ratio values plotted at 620 and 630 are shown at the same scale as values 610, but they have been offset along the y axis so that they can be clearly distinguished from one another. It can be seen that the raw instrument values 610 vary in accordance with the sample gas concentration variation. Indeed, the standard deviation for these measurements is 0.48 per mil. However, both the first $\delta_{13C}$ values calibrated without linear interpolation 620 and the second $\delta_{13C}$ values 630 calibrated with linear interpolation show significantly less variation than the raw instrument values. Moreover, the second $\delta_{13C}$ values 630 calibrated with linear interpolation have a standard deviation of 0.07 per mil, which is significantly less variation than the first $\delta_{13C}$ values 620 calibrated without linear interpolation, which have a standard deviation of 0.13 per mil and which show a small variation in time, matching that of the sample gas concentration.

Many variations on these techniques can be employed. In any embodiment, the portion 331, 332, 333, 334 need not be a final portion of the respective measurement time period 321, 322, 323, 324 and it can be 10%, 20%, 25%, 30%, 50%, 70%, 75%, 80%, 85%, 90%, 95% or 100% of the total. The portion can be adjusted and can vary between measurement time periods, for example dependent upon the rate of change of concentration or based on user preferences. Also, the length of the measurement time period can be changed (possibly dynamically), based on the rate of change of concentration or user preferences, if warranted. Where interpolation is used, a linear or non-linear interpolation may be possible. Various interpolation or curve matching techniques can be employed.

Whilst the invention has been described with the example of a $CO_2$ analysis system (i.e. with $CO_2$ as both sample and reference gas), it should be appreciated that any other gas that is susceptible to isotope ratio analysis, either by optical spectrometry or mass spectrometry or other spectrometry technique, could be employed. In those cases, the reference gas will not be $CO_2$ but will the same gas as the particular sample gas being analysed. Similarly, whilst the spectrometer that has been described is the preferred example of an optical spectrometer, it should be appreciated that a mass spectrometer or other spectrometer could equally be employed.

A list of some examples of analyte gases and some of their measurable isotope ratios is given below.

| Gas | Isotope ratio | | | |
| --- | --- | --- | --- | --- |
| $CO_2$, $CO$: | $^{13}C/^{12}C$ | $^{18}O/^{16}O$ | $^{17}O/^{16}O$ | |
| $CH_4$, other alkanes: | $^{13}C/^{12}C$ | $^{2}H/^{1}H$ | | |
| $N_2O$: | $\alpha$-$^{15}N/^{14}N$ | $\beta$-$^{15}N/^{14}N$ | $^{18}O/^{16}O$ | $^{17}O/^{16}O$ |
| $N_xO_y$: | $^{15}N/^{14}N$ | $^{18}O/^{16}O$ | $^{17}O/^{16}O$ | |

The carrier gas may be selected from: air, nitrogen, helium or argon, or mixtures of any two or more of the foregoing.

The invention claimed is:

1. A method of measuring an isotope ratio of a continuous sample in an isotope ratio spectrometer comprising:

a) measuring at least one sample isotope ratio over a measurement time period $t_s^n$ (n≥1) in the spectrometer;

b) measuring a sample concentration $c_s^n$ over at least a part of the measurement time period $t_s^n$ in the spectrometer;

c) selecting, using a processor, a reference gas concentration $c_{ref}^n$ for the spectrometer for reference to the sample measured during the measurement time period $t_s^n$, on the basis of the measured sample concentration $c_s^n$ to match the reference gas concentration $c_{ref}^n$ to the measured sample concentration $c_s^n$, and controlling the mix of a reference gas and a carrier gas to achieve the reference gas concentration $c_{ref}^n$;

d) measuring an isotope ratio of the reference gas at the selected reference gas concentration $c_{ref}^n$ in the spectrometer;

e) calibrating the at least one isotope ratio of the sample measured during the measurement time period $t_s^n$, having a sample concentration $c_s^n$, using the measured isotope ratio of the reference gas at the corresponding reference gas concentration $c_{ref}^n$; and f) determining a plurality of calibrated isotope ratios and a plurality of sample gas concentration measurements, each of the plurality of calibrated isotope ratios and the plurality of sample gas concentration measurements being for a different, respective time.

2. The method of claim 1, further comprising:

iteratively repeating steps (a) to (e) for n=n+1, n+2 . . . so that, during a certain measurement time period $t_s^n$ (n≥1), the selected concentration of the reference gas during that certain measurement time period $t_s^n$ is based upon the measured sample concentration during that certain measurement time period $t_s^n$; and wherein the step f) of determining the plurality of calibrated isotope ratios and the plurality of sample gas concentration measurements comprises associating the at least one calibrated isotope ratio and the measured sample concentration for each measurement time period $t_s^n$ (n≥1), with a time from the respective measurement time period $t_s^n$.

3. The method of claim 2, wherein the duration of a measurement time period $t_s^{n+1}$ that is subsequent to the certain measurement time period $t_s^n$, is set on the basis of a rate of change of sample concentration $c_s^n$ during the certain measurement time period $t_s^n$.

4. The method of claim 1, wherein the step d) of measuring at least one sample isotope ratio over the measurement time period $t_s^n$ in the spectrometer comprises measuring a plurality of sample isotope ratios over the measurement time period $t_s^n$ in the spectrometer and wherein the step f) of determining the plurality of calibrated isotope ratios and the plurality of sample gas concentration measurements comprises associating each of the plurality of sample isotope ratios measured over the measurement time period $t_s^n$ with a respective time from the measurement time period $t_s^n$.

5. The method of claim 1, wherein the step c) of measuring the isotope ratio of the reference gas at the reference gas concentration $c_{ref}^n$ in the spectrometer takes place during a reference time period $t_{ref}^n$ that is subsequent to the measurement time period $t_s^n$.

6. The method of claim 1, further comprising, before step a):

selecting a preceding reference gas concentration $c_{ref}^{n-1}$ for use in connection to a time period that is before the measurement time period $t_s^n$;

wherein the step c) of selecting a reference gas concentration $c_{ref}^n$ for the spectrometer for reference to the sample measured during the measurement time period $t_s^n$ is on the basis of the measured sample concentration $c_s^n$ during measurement time period $t_s^n$ and on the basis of the selected preceding reference gas concentration $c_{ref}^{n-1}$.

7. The method of claim 6, further comprising:
measuring the concentration of the reference gas at the selected preceding reference gas concentration $c_{ref}^{-1}$; and
calculating a correction factor based upon a ratio of the selected preceding reference gas concentration $c_{ref}^{n-1}$ to the measurement of the preceding reference gas concentration; and
wherein the step c) of selecting the reference gas concentration $c_{ref}^n$ comprises applying the calculated correction factor to the sample concentration $c_s^n$ measured over the at least part of the measurement time period $t_s^n$.

8. The method of claim 7, wherein the step of measuring the concentration of the reference gas at the selected preceding reference gas concentration $c_{ref}^{n-1}$ takes place during a preceding reference time period $t_{ref}^{n-1}$ that is prior to the measurement time period $t_s^n$.

9. The method of claim 6, wherein the step of selecting a preceding reference gas concentration $c_{ref}^{n-1}$ is on the basis of an anticipated sample concentration for the said measurement time period.

10. The method of claim 1, wherein the step b) of measuring the sample concentration $c_s^n$ over at least a part of the measurement time period $t_s^n$; comprises determining an average sample concentration over the at least part of the measurement time period $t_s^n$ and wherein the step e) of calibrating the isotope ratio of the sample uses the measured isotope ratio of the reference gas at the determined average sample concentration.

11. The method of claim 10, wherein the at least part of the measurement time period $t_s^n$ is the whole of the measurement time period $t_s^n$.

12. The method of claim 10, wherein the at least part of the measurement time period $t_s^n$ is only a last part of the measurement time period $t_s^n$.

13. The method of claim 1, further comprising:
measuring the isotope ratio of the reference gas at a preceding reference gas concentration $c_{ref}^{n-1}$ in the spectrometer during a preceding reference time period $t_{ref}^{n-1}$ that is before the measurement time period $t_s^n$ (n≥1); and
wherein the step e) of calibrating the at least one isotope ratio of the sample measured during the measurement time period $t_s^n$ uses the measured isotope ratio of the reference gas at the preceding reference gas concentration $c_{ref}^{n-1}$ and the measured isotope ratio of the reference gas at the measurement reference gas concentration $c_{ref}^n$.

14. The method of claim 13:
wherein the step d) of measuring at least one sample isotope ratio over the measurement time period $t_s^n$ in the spectrometer comprises measuring a plurality of sample isotope ratios over the measurement time period $t_s^n$ in the spectrometer; and
wherein the step e) of calibrating the at least one isotope ratio of the sample measured during the measurement time period $t_s^n$ comprises, for each of the plurality of sample isotope ratios:
identifying a respective sample characteristic for the respective sample isotope ratio;
determining a respective isotope ratio of the reference gas for the identified respective sample characteristic; and
calibrating the respective sample isotope ratio using the determined respective isotope ratio of the reference gas.

15. The method of claim 14, wherein the respective sample characteristic for the respective sample isotope ratio comprises a respective sample concentration for the respective sample isotope ratio.

16. The method of claim 15, wherein the step of determining a respective isotope ratio of the reference gas for the identified respective sample characteristic comprises interpolating between the measured isotope ratio of the reference gas at the preceding reference gas concentration $c_{ref}^{n-1}$ and the measured isotope ratio of the reference gas at the measurement reference gas concentration $c_{ref}^n$.

17. The method of claim 14, wherein the respective sample characteristic for the respective sample isotope ratio comprises a respective sample measurement time for the respective sample isotope ratio.

18. The method of claim 17, wherein the step of determining a respective isotope ratio of the reference gas for the identified respective sample characteristic comprises interpolating between the measured isotope ratio of the reference gas at the preceding reference time period $t_{ref}^{n-1}$ and the measured isotope ratio of the reference gas at the measurement reference time period $t_{ref}^n$.

19. The method of claim 1, wherein the continuous sample is derived from one or more of: ambient air; an open air source; a plant chamber; and a gas monitoring input.

20. A controller for a continuous sample isotope ratio spectrometer, the controller including a processor configured to
a) measure at least one sample isotope ratio over a measurement time period $t_s^n$ (n≥1) in the spectrometer;
b) measure a sample concentration $c_s^n$ over at least a part of the measurement time period $t_s^n$ in the spectrometer;
c) select, using a processor, a reference gas concentration $c_{ref}^n$ for the spectrometer for reference to the sample measured during the measurement time period $t_s^n$, on the basis of the measured sample concentration $c_s^n$ to match the reference gas concentration $c_{ref}^n$ to the measured sample concentration $c_s^n$, and control the mix of a reference gas and a carrier gas to achieve the reference gas concentration $c_{ref}^n$;
d) measure an isotope ratio of the reference gas at the selected reference gas concentration $c_{ref}^n$ in the spectrometer;
e) calibrate the at least one isotope ratio of the sample measured during the measurement time period $t_s^n$, having a sample concentration $c_s^n$, using the measured isotope ratio of the reference gas at the corresponding reference gas concentration $c_{ref}^n$; and
f) determine a plurality of calibrated isotope ratios and a plurality of sample gas concentration measurements, each of the plurality of calibrated isotope ratios and the plurality of sample gas concentration measurements being for a different, respective time.

21. An isotope ratio spectrometer configured to receive a continuous sample and comprising the controller of claim 20.

* * * * *

UNITED STATES PATENT AND TRADEMARK OFFICE
CERTIFICATE OF CORRECTION

PATENT NO.       : 9,874,513 B2                       Page 1 of 1
APPLICATION NO.  : 15/035736
DATED            : January 23, 2018
INVENTOR(S)      : Hans-Juergen Schlueter et al.

It is certified that error appears in the above-identified patent and that said Letters Patent is hereby corrected as shown below:

In the Claims

Claim 7, Column 19, Line 10:
Replace "reference gas concentration $C_{ref}^{-1}$"
With --reference gas concentration $C_{ref}^{n-1}$--

Signed and Sealed this
Twelfth Day of June, 2018

Andrei Iancu
*Director of the United States Patent and Trademark Office*